(12) United States Patent
Krämer et al.

(10) Patent No.: US 8,557,180 B2
(45) Date of Patent: Oct. 15, 2013

(54) SYSTEM AND METHOD FOR ANALYZING A SAMPLE LIQUID

(75) Inventors: Uwe Krämer, Ilvesheim (DE); Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1393 days.

(21) Appl. No.: 11/559,472

(22) Filed: Nov. 14, 2006

(65) Prior Publication Data

US 2007/0217950 A1 Sep. 20, 2007

(30) Foreign Application Priority Data

Nov. 15, 2005 (EP) ..................................... 05024897

(51) Int. Cl.
- *G01N 21/00* (2006.01)
- *G01N 35/02* (2006.01)
- *G01N 37/00* (2006.01)
- *G01N 21/01* (2006.01)

(52) U.S. Cl.
USPC ........... 422/66; 422/67; 422/68.1; 422/82.05; 422/400; 422/401; 422/402; 422/403; 422/404; 436/44; 436/46; 436/55; 436/165; 356/244

(58) Field of Classification Search
None
See application file for complete search history.

(56) References Cited

U.S. PATENT DOCUMENTS

| | | | |
|---|---|---|---|
| 4,071,315 A * | 1/1978 | Chateau | 436/518 |
| 4,790,979 A * | 12/1988 | Terminiello et al. | 422/56 |
| 4,867,946 A | 9/1989 | Hoechst | |
| 5,686,047 A | 11/1997 | Augstein | |
| 6,707,554 B1 | 3/2004 | Miltner et al. | |
| 2002/0192883 A1 | 12/2002 | Pan et al. | |

FOREIGN PATENT DOCUMENTS

| | | |
|---|---|---|
| DE | 198 19 407 | 11/1999 |
| EP | 0 693 688 | 1/1996 |
| WO | WO 2004/056269 | 7/2004 |

* cited by examiner

*Primary Examiner* — Neil N Turk
(74) *Attorney, Agent, or Firm* — Bose McKinney & Evans LLP

(57) ABSTRACT

The present invention provides a system for analyzing a sample liquid comprising a test tape having a plurality of test elements, a tape transport device which successively transports the test elements to a sample application site while advancing the tape, and a measuring device which scans the test elements loaded with sample liquid at a measuring site. The measuring site is located at a distance from the sample application site in the direction of tape movement. The tape transport is interrupted in order to exactly position a wetted area of the test elements carrying a sample liquid at the measuring site by means of a positioning device that responds to the presence of sample liquid on the test element.

13 Claims, 3 Drawing Sheets

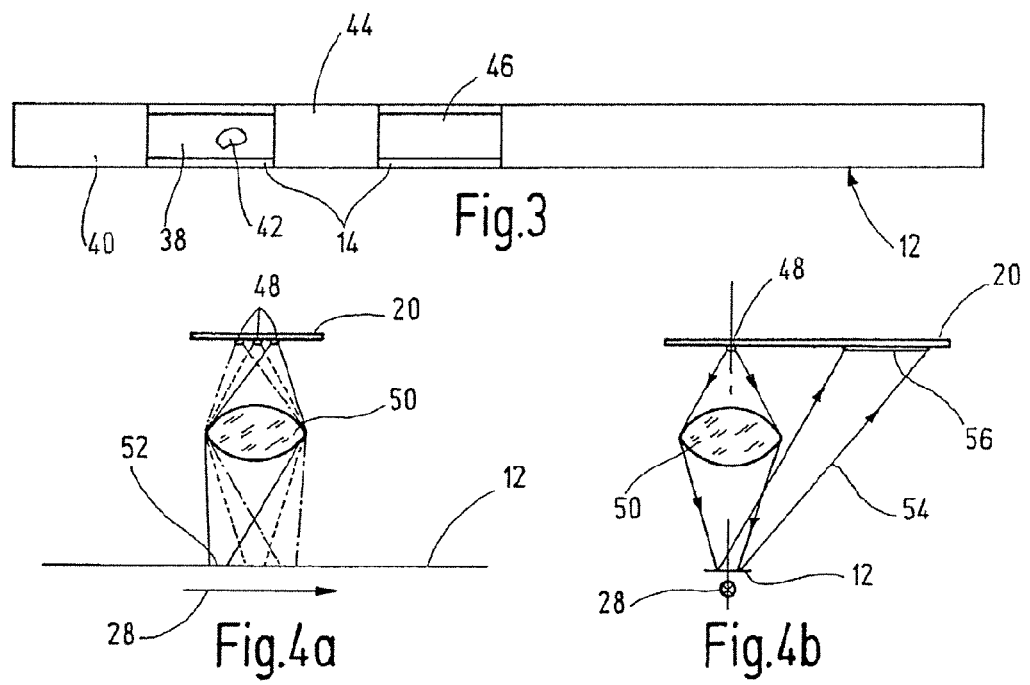

SYSTEM AND METHOD FOR ANALYZING A SAMPLE LIQUID

RELATED APPLICATIONS

This application claims priority to EP 05 024 897.0, filed Nov. 15, 2005.

BACKGROUND

The present invention relates to a system for analyzing a sample liquid, in particular, for blood glucose determinations, comprising a test tape having a plurality of test elements that is preferably stored in a tape cassette, a tape transport device which successively transports the test elements to a sample application site while advancing the tape, and a measuring device which scans the test elements loaded with sample liquid at a measuring site, wherein the measuring site is located at a distance from the sample application site in the direction of tape movement. The invention also relates to a method of using a device of the type having a tape cassette including a tape carrying a plurality of test elements.

WO 2004/056269 describes a test system for body fluids comprising a test tape for providing a plurality of test units that are applied to sections of a support tape in a compact hand-held device. In the case of blood sugar self-monitoring that usually has to be carried out several times daily this should impose the fewest possible handling steps on the affected person. A deflection of the test elements over a deflecting tip which at the same time constitutes the measuring site is provided in order to be able to meter the smallest possible amount of blood. In addition it is also mentioned that a measuring position at a distance from the collecting position allows reading optics or an electrochemical analytical unit to be separately positioned in the instrument.

U.S. Pat. No. 6,707,554 B1 describes a photometric analytical system for test elements in the form of test strips which are positioned by means of instrument stops. Several point light sources are provided to illuminate different areas of the detection zone on the test strip in order to compensate for tolerances wherein it is then intended to make a selection on the basis of the signals that are obtained.

SUMMARY OF THE INVENTION

Embodiments of the present invention further improve the systems known in the prior art and in particular enable optimization of instrument design and enable a reliable measurement with the smallest possible amounts of sample.

The present invention is based on the idea of enabling a directed measurement of test elements without the need for mechanical positioning elements. Accordingly, embodiments of the invention provide a positioning device which responds to the presence of sample liquid on the test element that is active at the time and controls the tape transport device in order to interrupt tape transport to position a wetted area of the test elements carrying sample liquid at the measuring site. In this manner, it is possible to provide a larger test area for sample application without requiring the whole area to be covered. Hence, especially for blood sugar measurements, microscopic amounts of blood are sufficient which can be collected in a painless manner while creating additional comfort due to an integrated lancing unit because the site of collection is not displaced by a measuring unit. The construction of the system is simplified and the constructional space is better utilized by the transport positioning and it can be ensured that an accurately targeted detection takes place even with a variable amount of applied sample.

The positioning device advantageously comprises a control unit coupled to a tape drive for a targeted stop of the tape at the measuring site and is in particular realized by a program routine of a microprocessor. Another improvement is achieved by means of the positioning device having at least one optical detection unit which responds when the wetted area passes through.

In order to ensure the sample is accurately centered, it is advantageous when the positioning device has two light sources aligned with (directed to) tape passage positions or spots located before and after a zone of the measuring device that detects the useful signal. This can be achieved simply by the positioning device having several light emitting diodes that are imaged or directed consecutively along a path the test tape travels. The diodes produce consecutive light spots on the tape in the direction of tape movement by common collection optics.

The positioning device advantageously has at least one photosensor for scanning the test elements preferably by reflectometry. In this connection, it is advantageous when the photosensor detects a blank value in an unwetted area of the test field and a target value that is different therefrom in the wetted area.

In order to meet the high requirements made on the quality of signal detection, it is advantageous when the measuring device has a detector that is separate from the positioning device for detecting the useful signals for the detection of an analyte in the sample liquid.

The test elements are advantageously formed as flat test fields on the test tape that are preferably in the form of a reagent layer. The test fields can have a reference area for a blank value measurement that is kept free from the sample liquid by a liquid barrier.

The fine positioning can also be accomplished by the test tape being provided with a tape marking, in particular, with a line scale, marking holes or color marks at least on sections of the tape and by the positioning device having a scanning means, in particular, a light barrier to scan the tape marking while the tape is advanced. The line scale or the marking holes can be introduced by a laser during tape manufacture.

In order to reduce the required amount of sample, the wetted area of the test elements preferably has a diameter of less than 5 mm, more preferably, of 1 to 2 mm.

In order to create sufficient free space for the measuring device, it is advantageous when the measuring site is positioned at a distance of 5 mm to 5 cm from the sample application site.

In another embodiment of the system design, especially for blood sugar measurements, a lancing device is positioned at the sample application site for piercing a body part, preferably through the test tape.

The tape transport is controlled by a positioning device that responds to the presence of sample liquid on the test element in order to position a wetted area of the test element carrying a sample liquid at the measuring site.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein:

FIG. 3 is a top view illustrating a section of test tape provided with test element;

FIGS. 4a and 4b illustrate two diagrammatic side views of the positioning device aligned with the test tape;

FIGS. 5a thru 5e illustrate different wettings of a test field with the corresponding reflectance signals.

Corresponding reference characters indicate corresponding parts throughout the several Figures.

DETAILED DESCRIPTION

Figure 1:
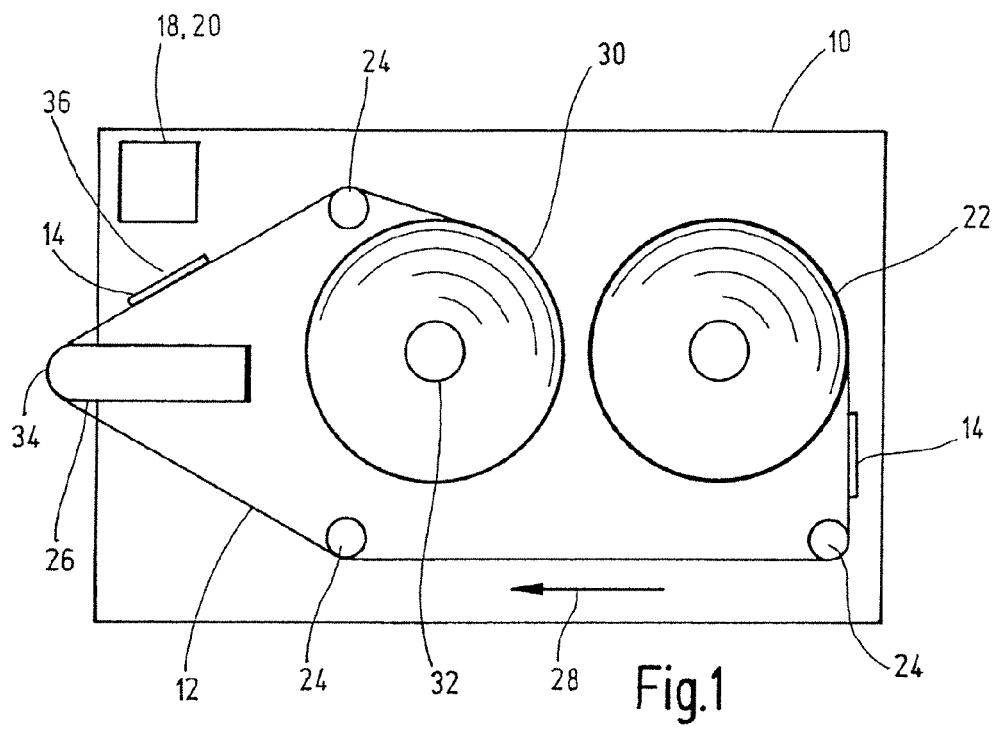
FIG. 1 is a schematic plan view illustrating a test tape system for blood glucose determination.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The test system shown in the drawings includes a test tape 12 having a plurality of test elements 14 located thereon which is inserted into a hand-held device 10 as a cassette, a transport device 16 for tape transport, a measuring device 18 for optically analysing the test elements 14 and a positioning device 20 to position the test fields 14 in the detection area of the measuring device 18.

Figure 2:
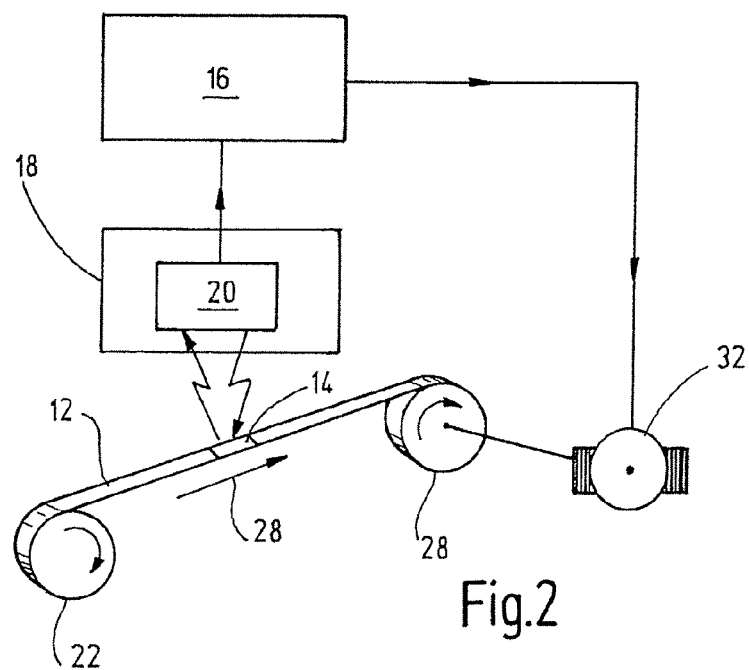
FIG. 2 is a diagrammatic view in partial perspective illustrating a positioning device for positioning the test tape at the site of measurement.

As illustrated in FIGS. 1 and 2, the test tape 12 can be pulled from a supply spool 22, pulled over various deflector rollers 24 and a deflector head 26, and advanced along a path indicated by arrow 28, i.e., in the direction of tape movement (arrow 28), and then wound onto a take-up reel 30. The tape is advanced (along path 28) by a motorized tape drive 32 which engages the take-up reel 30. Appropriate tape stops can be used to apply body fluid (blood) selectively to the test elements 14 in the area of the deflector head 26 at a sample application site and subsequently to optically scan them inside the instrument at the measuring site 36 by means of the measuring device 18.

As shown in FIG. 3, the test elements 14 are provided in the form of flat test fields composed of a reagent layer 38 which is applied to a transparent thin support tape 40. When a drop of blood is applied, the reagent layer 38 reacts to an analyte such as glucose in the sample fluid by producing a change in color, thus enabling an optical detection using the measuring device 18.

It is desirable for the user to be required to apply as little blood as possible, yet at the same time have available a large application zone 38. As a result, the area 42 that is wetted with blood or sample liquid can vary from measurement to measurement, and a positioning device 20 comprising a microprocessor ensures that the wetted area 42 is accurately detected at the measuring site 36 that is distant from the application site 34. For this purpose, the tape drive 32 is appropriately actuated such that positioning is achieved by interrupting the transport without requiring additional mechanical elements. In addition to the application zone 38, the test field 14 has a reference area 46 for a blank value measurement that is separated by a hydrophobic liquid barrier 44.

FIG. 4 illustrates the fine positioning of the wetted area 42 at the measuring site 36 by means of a photometric positioning device 20. The side view of FIG. 4a shows three light-emitting diodes 48 that are arranged in succession in the direction of tape movement and are imaged or directed consecutively on the passing tape 12 as corresponding light spots 52 by a collecting lens 50. In other words, the three diodes 48 are directed to three successive and adjacent spots on the path that the test tape travels. The spacing of the outer LEDs 48 is of the order of magnitude of the usual dimensions of the wetted zone 42, i.e., in a range of a few millimeters. The view of FIG. 4b in the direction of tape movement shows that the light 54 that is irradiated by the light-emitting diodes 48 and that is diffusely reflected by the test elements 14 on the test tape 12, is detected laterally outside of the direct reflection by a detector or photosensor 56 of the positioning device 20. In order to allow an assignment of the signals obtained using only one sensor 56, the LEDs 48 can be actuated separately from one another. In principle, it is possible that the sensor 56 is also used to detect the useful signal in addition to the presence of the wetted area. However, in order to meet the various requirements it is expedient to use a separate detector for this purpose.

FIG. 5 shows the spatial correlation of the various output signals of the sensor 56 to the respective wetted states of the test field 14 which are each shown above. When the test field 14 is completely dry, i.e., sample liquid has not been applied to the reaction area 32 and reference area 46, a blank value L is detected in both areas (FIG. 5a). In the case of the central wetting of the area 38 shown in FIG. 5b a lower reflectance value B is measured there corresponding to a color change in the reaction layer. FIGS. 5c and 5d show the situation of a wetting of the margin at the start and end of the reaction area 38, whereas a wetting of the whole area is shown in FIG. 5e.

It should also be noted that the test tape 12 can be provided with a puncture opening 58 located before the test element 14 for a lancing unit arranged in the area of the sample application site 34. Thus, with a standardized instrument it is possible by means of the lancing unit to collect capillary blood, for example, from a finger, to pick up blood at the sample application site 34 with a test element 14 by advancing the tapes and subsequently to position the respective test element at the measuring site 36 by advancing the tape further.

In this connection, the fine positioning can be achieved by means of the described row of light-emitting diodes 48 according to FIG. 4. When the reference area 46 passes through the first light spot 52 positioned along path 28 (generated by the right light-emitting diode 48 in FIG. 4a) the blank value L is detected and stored for comparison. When the wetted area 42 arrives at spot 52, the applied blood is detected by a lowered plateau or target value B of the reflectance which is less than L but larger than zero. When this value rises again, a control unit of the positioning device 20 interrupts the tape drive 32 such that the area 42 wetted with blood is located in the spot of the beam area of the middle LED 48, which can then also be used to carry out the actual test measurement. In order to further increase the reliability, a third light-emitting diode 48 can be provided (the left LED in FIG. 4a) which, if there is an additional response to blood, ensures that the entire detection area for useful signals illuminated by the middle LED is located in the test field area 42 wetted with blood.

Figure 6:
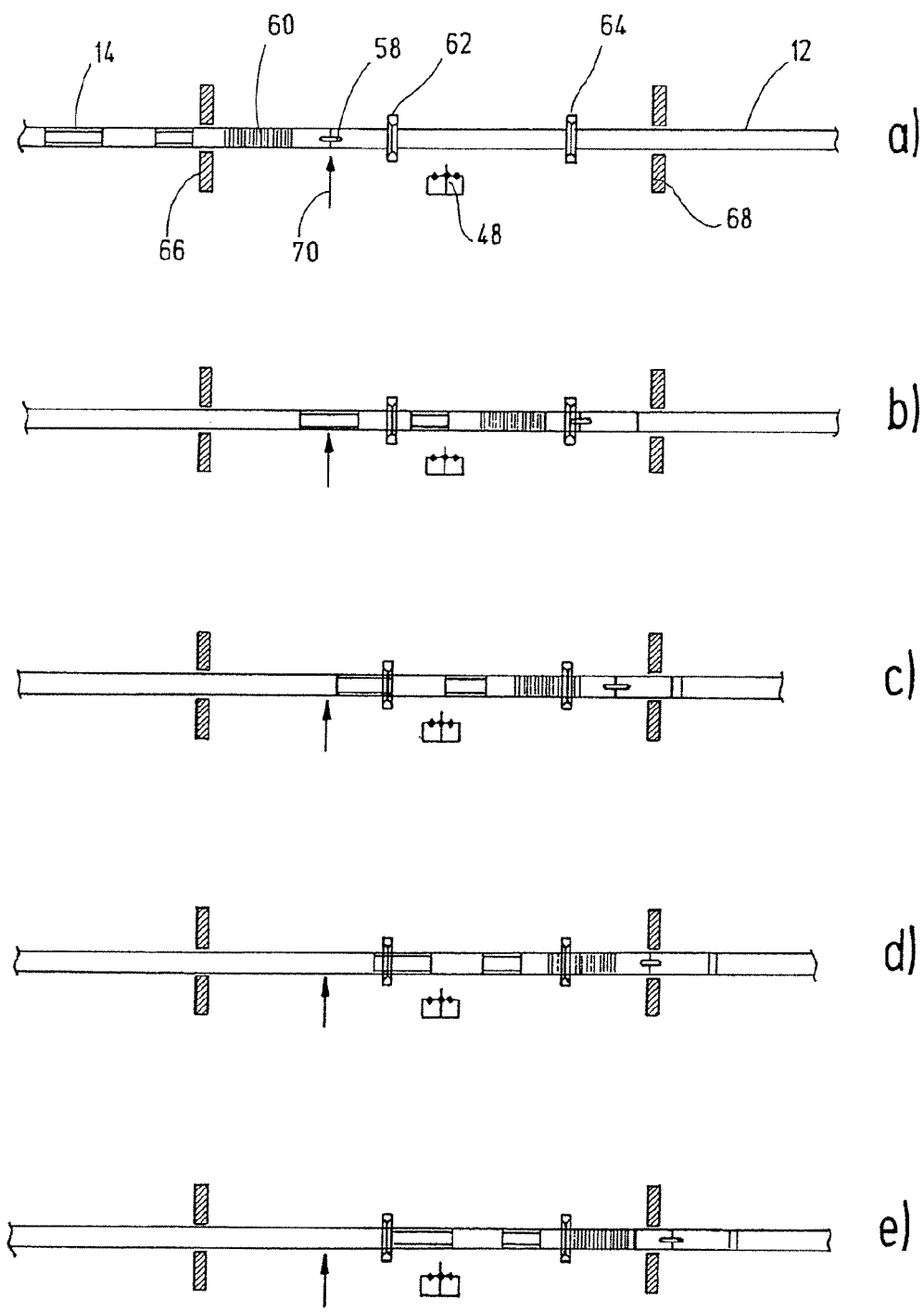
FIGS. 6a thru 6e illustrate another embodiment of a positioning device illustrating a section of test tape in various positions in its advancement.

In the embodiment shown in FIG. 6 the same parts are labelled with the same reference numerals as described above. A line scale 60 is additionally applied to the test tape 12 at a defined distance from a respective test element 14. In this case the positioning unit 20 comprises two light barriers 62, 64 to scan the test tape 12 as it passes over a housing edge 66 or seal 68. Blood is collected at the sample application site by lancing unit 70 (FIG. 6*a*) and subsequently applied to the test field 14 after appropriate tape advancement (FIG. 6*b*). In the course of further tape advancement, the start of the wetted area 42 is detected by a first light barrier 62 (FIG. 6*c*). At the same time the respective tape position is determined at the second light barrier 64 the line scale 60. Optionally, the end position of the wetted area can be determined according to FIG. 6*d*. The required forward movement for an exact positioning of the measuring device 18 is then calculated in the control unit of the positioning device 20 on the basis of the determined tape positions and executed by corresponding further scanning of the scale 60 and control of the tape drive 32 such that an accurate point measurement is possible in the position to which the wetted area has been moved according to FIG. 6*e*.

In addition to blood, it is also possible to analyze other sample or body fluids, in particular, interstitial fluid, in the manner described above.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A system for analyzing a sample liquid having an analyte, comprising:
    a test tape having a plurality of test elements;
    a tape transport device which advances the test tape to successively transport the test elements to a sample application site at which the test elements are loaded with sample liquid to form a wetted area whose location on the test elements can vary from measurement to measurement, the tape transport device also advancing the test tape to successively transport the test elements to a measuring site at which the test elements are positioned for the detection of the analyte, the measuring site being spaced from the sample application site in the direction of tape movement;
    a measuring device configured to detect an analyte in the test elements that are loaded with the sample liquid; and
    a positioning device associated with the tape transport device and configured to detect the presence of the wetted area on the test elements as the test tape is advanced, the positioning device comprising a control unit, the control unit configured to respond to the detection of the wetted area and configured to interrupt the tape transport when the wetted area of the test elements is determined by the positioned device to be positioned at the measuring site, whereby the location of the test elements relative to the measuring site may vary from measurement to measurement as a function of the location of the wetted area on the test elements.

2. The system of claim 1, wherein the control unit is coupled to a tape drive.

3. The system of claim 1, wherein the positioning device comprises at least one optical detection unit which responds when the wetted area arrives at the measuring site.

4. The system of claim 1, wherein the positioning device comprises two light sources directed to first and second spots, respectively, along a path the test tape travels, the first spot being positioned in front of a zone of the measuring device that detects the useful signal, the second spot being positioned behind the zone.

5. The system of claim 1, wherein the positioning device comprises a plurality of light-emitting diodes directed to consecutive spots on the path the test tape travels.

6. The system of claim 1, wherein the positioning device comprises at least one photosensor for scanning the test elements.

7. The system of claim 1, wherein the positioning device is configured to detect a blank value in an unwetted area of the test field and a target value that is different therefrom in the wetted area.

8. The system of claim 1, wherein the measuring device comprises a detector that is separate from the positioning device for detecting a signal that is representative of presence or concentration of an analyte in the sample liquid.

9. The system of claim 1, wherein the test elements comprise flat test fields in the form of a reagent layer on the test tape, the test fields having a reference area for a blank value measurement.

10. The system of claim 1, wherein the test tape comprises a line scale, marking holes or color marks and the positioning device comprises a scanner and a light barrier to scan the tape markings while the tape is advanced.

11. The system of claim 1, wherein the wetted areas of the test elements have a diameter of less than 5 mm.

12. The system of claim 1, wherein the measuring site is positioned 5 mm to 5 cm from the sample application site.

13. The system of claim 1, further comprising a lancing device positioned at the sample application site for piercing a body part.

* * * * *

UNITED STATES PATENT AND TRADEMARK OFFICE
CERTIFICATE OF CORRECTION

PATENT NO. : 8,557,180 B2  
APPLICATION NO. : 11/559472  
DATED : October 15, 2013  
INVENTOR(S) : Krämer et al.

Page 1 of 1

It is certified that error appears in the above-identified patent and that said Letters Patent is hereby corrected as shown below:

In the Claims:
Claim 1, column 6, line 4, the phrase "by the positioned device" is deleted and replaced with --by the positioning device--.

Signed and Sealed this
Fourth Day of February, 2014

Michelle K. Lee
*Deputy Director of the United States Patent and Trademark Office*